United States Patent [19]

Virta et al.

[11] Patent Number: 4,741,007
[45] Date of Patent: Apr. 26, 1988

[54] PANORAMIC X-RAY, TOMOGRAPHY ESPECIALLY FOR DENTAL PHOTOGRAPHY

[75] Inventors: Arto Virta, Vantaa; Pekka Strömmer, Espoo, both of Finland

[73] Assignee: Planmeca Oy, Finland

[21] Appl. No.: 868,724

[22] Filed: May 30, 1986

[30] Foreign Application Priority Data

May 31, 1985 [FI] Finland ................................ 852208

[51] Int. Cl.$^4$ .............................................. A61B 6/04
[52] U.S. Cl. ........................................ 378/39; 378/38; 378/40
[58] Field of Search .................. 378/38, 39, 40, 15

[56] References Cited

U.S. PATENT DOCUMENTS

| | | | |
|---|---|---|---|
| 3,737,660 | 6/1973 | Ando et al. | 378/39 |
| 4,589,122 | 5/1986 | Nieminen | 378/39 |

FOREIGN PATENT DOCUMENTS 0165139 12/1981 Japan .................................... 378/40

*Primary Examiner*—Janice A. Howell
*Assistant Examiner*—David P. Porta
*Attorney, Agent, or Firm*—Steinberg & Raskin

[57] ABSTRACT

A panoramic tomography X-ray apparatus comprises a fixed frame to which another rotary frame is suspended, the rotary frame having an X-ray tube at one end thereof and a film cartridge device for X-ray film at an opposite end thereof. Drive mechanism for turning the rotary frame in a substantially horizontal plane is provided, for taking a panoramic X-ray photograph. The drive mechanism comprise a drive and guide groove which has straight side sections and a curved section connecting the side sections together and a drive unit also comprising a drive wheel which, when rotated by the drive unit, turns the rotary frame. The rotary frame is suspended from the fixed frame by a crank mechanism which is joined to both the rotary frame and to the fixed frame through respective sets of bearings. The drive and guide mechanism along with the crank mechanism interact in such a manner that, in the front area of a dental arch, i.e. when the corresponding curved section of the guide and drive groove is in operation, the rotary frame turns around one axis of the crank mechanism, while in the side areas, when guided by the straight sections of the drive and guide groove, the rotary frame simultaneously turns about two axes of the crank mechanism.

19 Claims, 6 Drawing Sheets

PANORAMIC X-RAY, TOMOGRAPHY ESPECIALLY FOR DENTAL PHOTOGRAPHY

BACKGROUND OF THE INVENTION

The present invention relates to a panoramic tomography X-ray apparatus, especially for dental photography. This apparatus comprises a fixed frame, to which another rotary frame having an X-ray tube at one end and a film cartridge device for X-ray film at the other end, is suspended, e.g. through bearings. An object to be photographed, e.g. a patient, can be positioned between the X-ray tube and the film cartridge. The apparatus has a drive mechanism, by means of which the suspended rotary frame is rotated in a plane, preferably a horizontal plane, for taking panoramic X-ray photographs. The present invention is also directed to a method for taking panoramic photographs, such as X-rays of teeth.

The design and operating principle of most panoramic X-ray apparatus involve turning the X-ray path about the head of a patient, in such a manner that the dental arch will be photographed as a flat picture on a moving film.

In order to make the object being photographed sharp and the structures in front and behind the object invisible by "fogging" out of focus, the lateral velocity of the film with regard to the ray bundle must be equal to the sweep velocity of the ray bundle in the object multiplied by the magnification ratio. The magnification is determined by the ratio of the distance between the focus and the film, to the distance between the focus and the object.

The thickness of the layer being photographed sharply, is directly proportional to the distance of the instantaneous center of rotation from the film plane, and inversely proportional to the magnification and to the width of the ray bundle. A singular consideration, from the point of view of how the object will be represented, is how the focus, the object, and the film level are located with respect to one another. The instantaneous center of rotation is significant only through the sweep velocity.

It is possible to form the basic equation of panoramic photography, based on what has been outlined above: $V_1/V_0 = L_1/L_0$, and
$V_0 = \omega r$, where
$L_0$ = the distance from the focus F to the point being photographed a given moment,
$L_1$ = the distance from the focus F to the film level,
$\omega$ = the angular velocity of the rotary movement about the center of rotation,
$r$ = the distance of the point being photographed from the instantaneous center of rotation, and
$v_1$ = the velocity of an image point on the picture level (film level).

The most important objects of photography by a panoramic tomography X-ray apparatus, are the dental arch and the temporomandibular joints (there are other important objects of photography too). A fixed center of rotation must be abandoned in order to generate as useful a projection as possible of the object, and the least questionable mechanical arrangement. Moving the position of the center of rotation depends, among other factors, on the following:

orthogonality, aimed at preventing adjacent teeth at any point of the dental arch from being photographed on top of one another. Therefore, the ray bundle must sweep the object as perpendicularly as possible, i.e. orthogonally against the dental arch;

constant magnification, i.e. the magnification must be the same all over the dental arch, with the distance from the layer being photographed to the film level being maintained constant throughout the entire rotation;

evenness of movement, which has been difficult to maintain since it has been necessary to move the instantaneous center of rotation during the exposure. The projection must be such that the instantaneous center of rotation may move without discontinuities which could create excessive acceleration, thus harming the quality of the picture; and minimization of the radiation load to the patient, for which the projection must be such that excessive radiation will not be applied to a single point on the patient.

It should be possible to manufacture an X-ray source of the apparatus and the rotary mechanism for the film cartridge to create the projection meeting the requirements specified above, within reasonable cost so that there will be no play or other inaccuracies detrimental to the photography. In order to create the desired projection, the mechanism must therefore move the center of rotation in a horizontal plane. The mechanism must also vertically support the entire equipment. Therefore, the vertical bearing system must be stable and without play in order to provide a good photograph.

In the prior art, orthogonality has been satisfactorily maintained in the dental arch area. However, almost no attention has been paid to the temporomandibular joint. With commercially-available apparatus, it is not possible to maintain the magnification ratio constant, a shortcoming which can be seen in the tomography exposures in a manner such that the front part of the dental arch and/or the entire dental arch are photographed with noticeably higher magnification ratios, than the temporomandibular joints. The reason for this, is that in the known apparatus, the film cartridge comes much closer to the object being photographed in the side region, than in the frontal area.

Additionally, the rotary movement in the prior art has been such that, during the entire exposure, the center of rotation is located in the area outlined by the temporomandibular joints or near this area, resulting in a high local radiation load in this particular area. For the same reason, the temporomandibular joints are photographed at an oblique angle, which is an obvious drawback for diagnostic purposes.

The most relevant prior art will now be described in connection with the following references:

Finnish patent application No. 833,754 illustrates panoramic tomography equipment, in which the constant magnification problem is solved in one manner. This reference, however, takes no position on how to produce the projection. A solution in accordance with British Pat. No. 1,594,499, referred to in the above Finnish application, produces a projection in which the temporomandibular joints are photographed at a highly oblique angle (not orthogonally). In an apparatus in accordance with the above application, the movement parallel with the ray bundle, required by constant magnification, is created by a linear bearing system which is structurally a difficult and expensive solution.

U.S. Pat. No. 4,264,820 deals with an X-ray method and apparatus, in which attention has been paid to the constant magnification problem. However, even this patent has no view on the projection to the temporomandibular joint area. Orthogonality in this reference is only examined in the dental arch area. Two systems are described for attaining constant magnification. However, the following drawbacks can be perceived in both these systems:

so called revolving slides move in grooves, which makes it very difficult, even impossible, to operate without play;

the stability of the apparatus in the horizontal plane is questionable at such points of the rotary movement in which the revolving slide guide grooves are at an unfavorable angle towards one another;

a method of transmitting rotary movement leads to improper rotation of the drive wheel (i.e. axial displacement);

in the particular arrangement described in this patent, in which one of the revolving slide grooves is replaced by a crank, the control of the revolving cranks in the groove is critical from the point of view of the result of the exposure, since the revolving slide does not stably follow either one of the groove edges; and in the last-mentioned particular arrangement of the above reference, transmission of the rotary movement can be arranged so that the drive will be proper and the drive wheel runs along a circular track, however the design will be complex, bulky, and expensive.

SUMMARY OF THE INVENTION

Accordingly, it is an object of the present invention to provide an apparatus in which the problems discussed above are solved by means of an arrangement that is mechanically simple and feasible.

It is also an object of the present invention to provide such an apparatus in which there are no detrimental mechanical plays or similar inaccuracies.

It is another object of the present invention to provide such an apparatus in which the orthogonality described above is carried out both in the dental arch area, and in the rear part of the jawbone up to the temporomandibular joints, with good sharpness.

It is a further object of the present invention to provide such an apparatus in which the magnification is constant over the entire image field.

It is an additional object of the present invention to provide such an apparatus in which the film can be brought closer to the patient or object being photographed, in order to reduce the magnification ratio without any risk of the film cartridge hitting the patient or object.

It is still another object of the present invention to provide such a device or apparatus in which the maximum localized radiation load can be substantially reduced.

These and other objects are attained by the present invention which is directed to a panoramic tomography X-ray apparatus, especially for dental photography, having a fixed frame and a rotary frame suspended from the fixed frame, the rotary frame having an X-ray tube at one end thereof and a film cartridge device for X-ray film at an opposite end thereof. An object to be photographed may be positioned between the X-ray tube and the film cartridge, with the rotary frame being situated to be rotatable in a plane for taking panoramic X-ray photographs.

More particularly, the apparatus comprises drive means for rotating the rotary frame about the plane. The drive means comprise a drive and guide device which can be a groove or rail that is substantially symmetrical with a center plane of the apparatus. The drive and guide device has substantially straight side sections, and a curved section interconnecting the side sections.

A drive unit is situated to interact with the drive and guide device. A drive wheel of the drive unit turns the rotary frame. Crank means are provided for suspending the rotary frame from the fixed frame, the crank means being connected at one axis with the rotary frame adjacent the X-ray tube end, and at a second axis with the fixed frame at an opposite end. When the rotary frame is substantially centered in the apparatus, these two axes of the crank means are substantially positioned along the center plane of the apparatus.

The drive means and crank means are situated with respect to one another, and so interact that when the drive unit passes around the curved section of the drive and guide device, the rotary frame turns about the second axis of the crank means. When the drive unit is guided along the straight sections of the drive and guide device, the rotary frame simultaneously turns about both the first and second axis of the crank means.

The present invention is also directed to a method for taking panoramic photographs, such as X-rays of teeth, which comprises situating film and a photographic energy source on opposite sides of an object to the photographed, rotating the source about a center of rotation substantially situated on a center plane of the rotational arc, and gradually shifting the center of rotation as the source moves away from the center plane.

In the present invention, the drive and guide device comprises a drive and guide groove or corresponding rail system, which is substantially symmetrical with respect to the center plane of the apparatus, and which has substantially straight side sections and a curved section interconnecting the side sections with one another. The drive unit is installed to interact with the drive and guide groove or similar rail system, and comprises a drive wheel which, when rotated by the drive unit, turns the rotary frame. The rotary frame is suspended from the fixed frame by the crank means, which is, at the X-ray tube end, joined to the rotary frame by means of a bearing, and at an opposite end, joined to the fixed frame by means of another bearing (i.e. along the respective first and second axis thereof) so that, when the rotary frame is in the central position, the two opposite axis (e.g. journal pins) of the crank means are positioned along the vertical center plane of the apparatus.

The drive unit, drive and guide device, and the crank means are disposed to interact with one another in such a manner that, in the frontal area of a dental arch or similar object, i.e. when the corresponding section of the guide and drive groove or rail is being contacted by the drive unit, the rotary frame turns about a front journal pin, i.e. the journal pin located on the side of the X-ray film cartridge. When the drive unit contacts the side sections of the drive and guide device, i.e. when guided by these straight sections of the drive and guide groove or rail system, the rotary frame simultaneously turns about both journal pins or similar structure of the crank means.

BRIEF DESCRIPTION OF THE DRAWINGS

The present invention will now be described in greater detail, with reference to certain exemplary embodiments illustrated in the drawings, to which the present invention is not intended to be confined. In the drawings.

DESCRIPTION OF THE PREFERRED EMBODIMENTS

Figure 1:
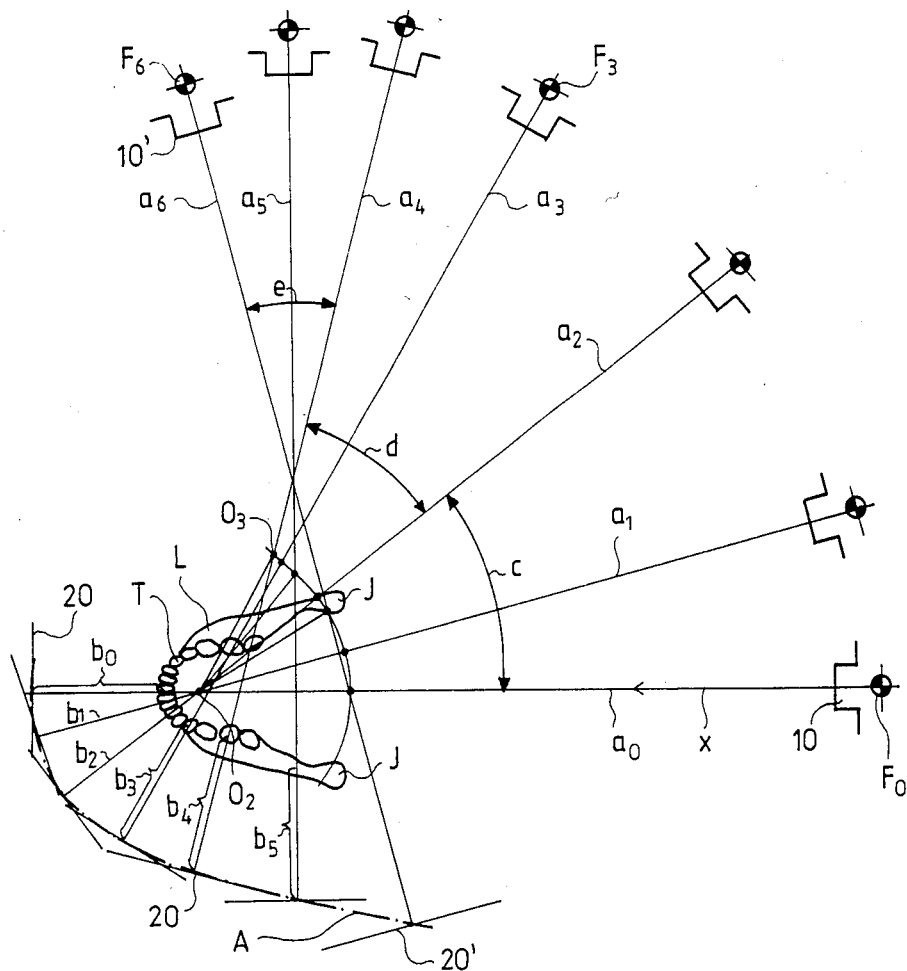
FIG. 1 is a schematic illustration of a projection produced by the present invention.

FIG. 1 illustrates photographing geometry and projection accomplished in accordance with the present invention. In this figure, the X-ray tube 10 has a focus $F_0$ to $F_6$ in different positions as illustrated. The X-ray tube 10 transmits an X-ray bundle X through teeth T and jawbone L onto a film 20, along the line a. In FIG. 1, the passage of the X-ray X is illustrated in seven different positions, i.e. $a_0$ to $a_6$. In an end position, the X-ray tube is denoted with reference 10', the film denoted with reference 20', and the focus of the tube 10' being denoted by $F_6$. The joints of the jawbone L are marked with the reference character J.

In the front area of the dental arch, represented by the space between the rays $a_0$ and $a_2$ (sector c), a rotary frame or arm 11, supporting the X-ray tube 10 on one end and the film 20 at the other end thereof, rotates over a horizontal plane about a vertical axis $O_2$. Between the rays $a_2$ and $a_4$ (sector d), the center of rotation smoothly moves along a curved path to the vertical axis $O_3$, after which the vertical axis draws further away from the center axis $a_0$ (C—C in FIG. 4).

With the geometry and positioning illustrated in FIG. 1, orthogonality of the representation is attained with excellent accuracy, in both the front dental arch area, and also in the side areas and in the rear part of the jawbone L up to the joints J. Magnification is also constant over the entire image field. This is proven, for instance, by the fact that the distance $b_0$–$b_5$ of the film 20 from the photographed layer, is substantially constant over the entire path. Since the distant $b_0$–$b_5$ is constant, the film 20 can be brought closer to the patient P (FIG. 5) in order to reduce the magnification ratio without a risk of the film cartridge hitting the patient. The described geometric positioning also results in a substantially lower level of radiation, as compared with the prior art, since the lateral centers of the rotation of the frame 11 are situated outside of the patient.

Figure 2:
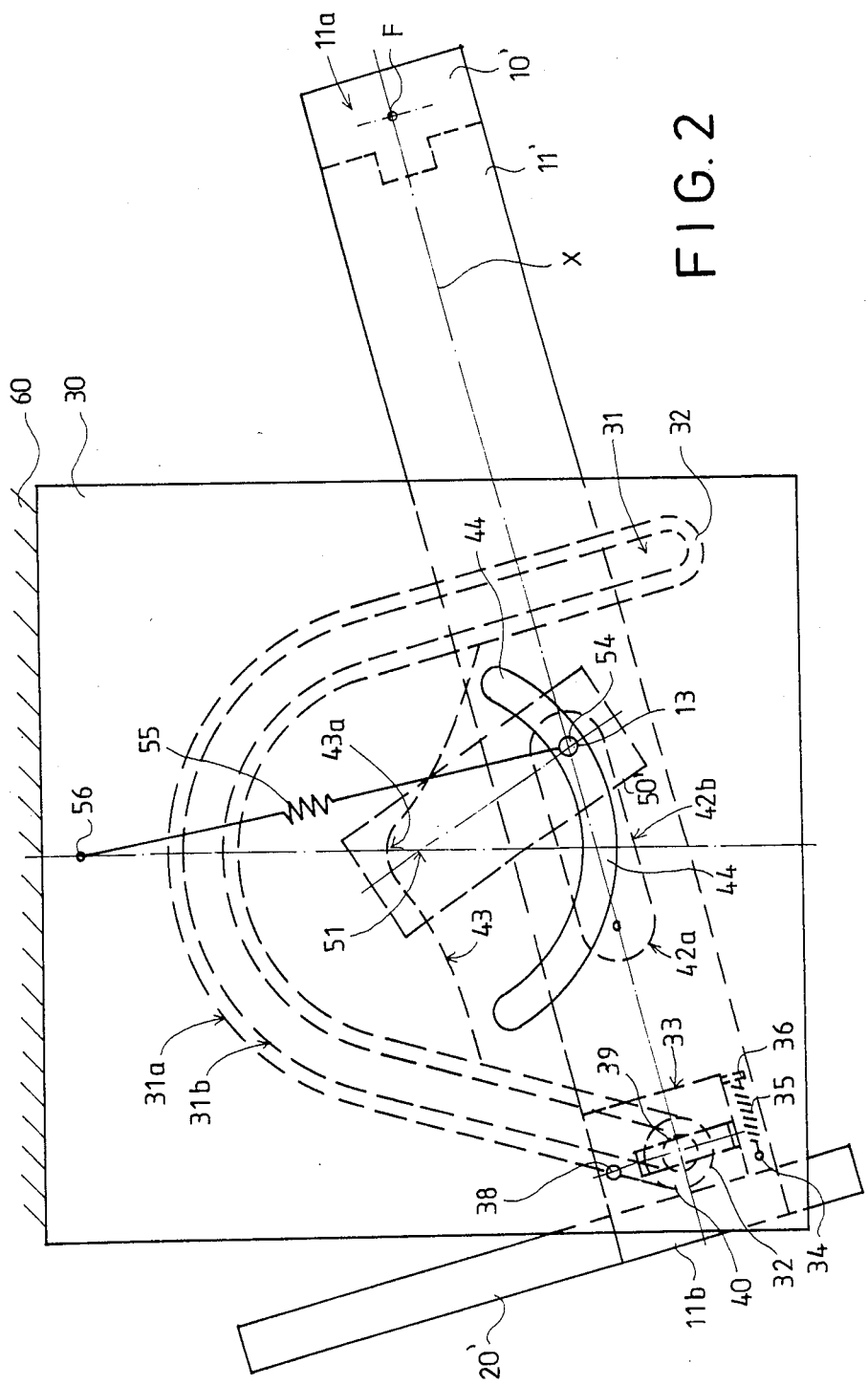
FIG. 2 is a schematic plan view of the present invention, at an end position thereof.
Figure 3:
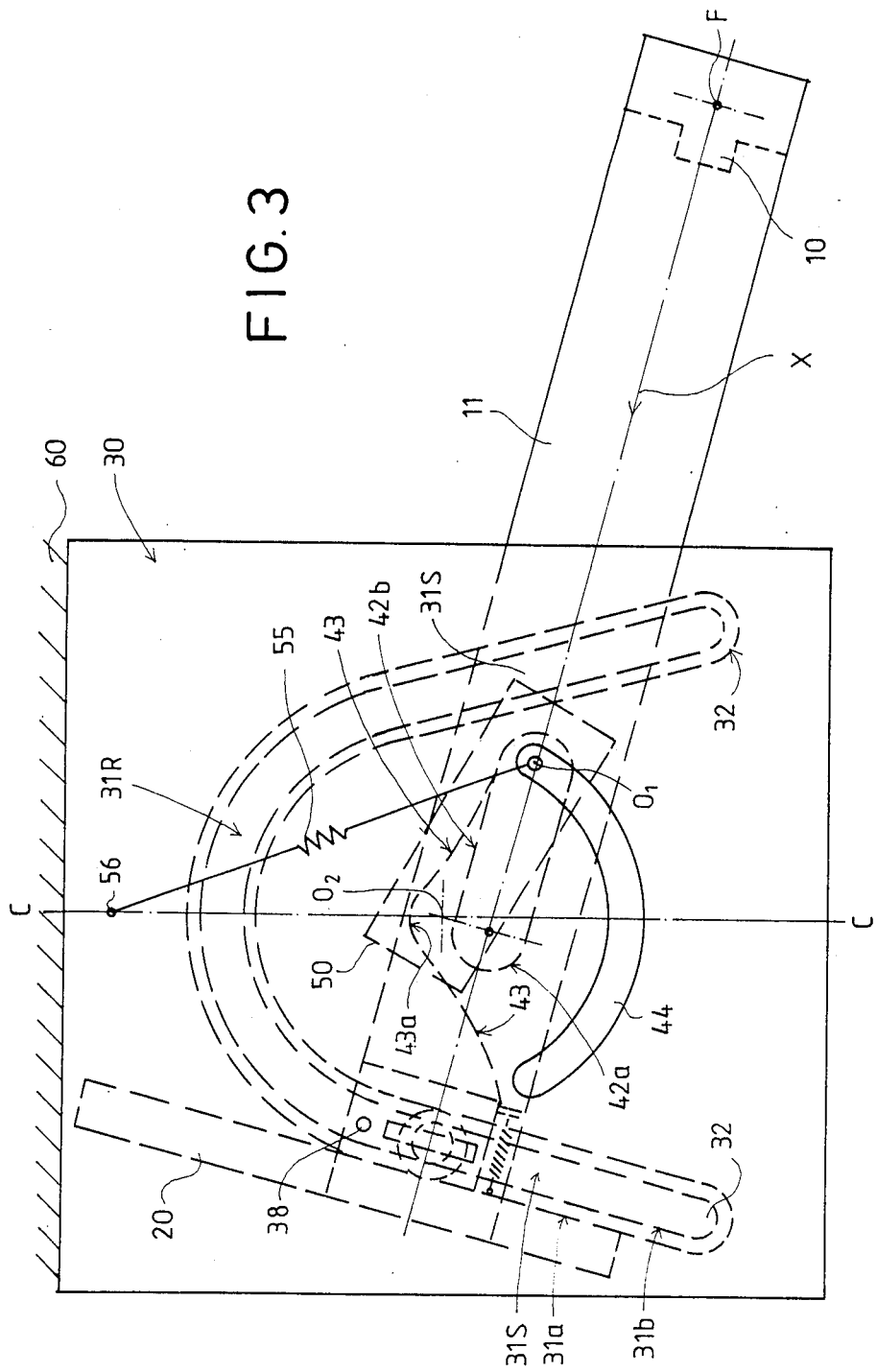
FIG. 3 is a view similar to FIG. 2, illustrating an intermediate position of the present invention.
Figure 4:
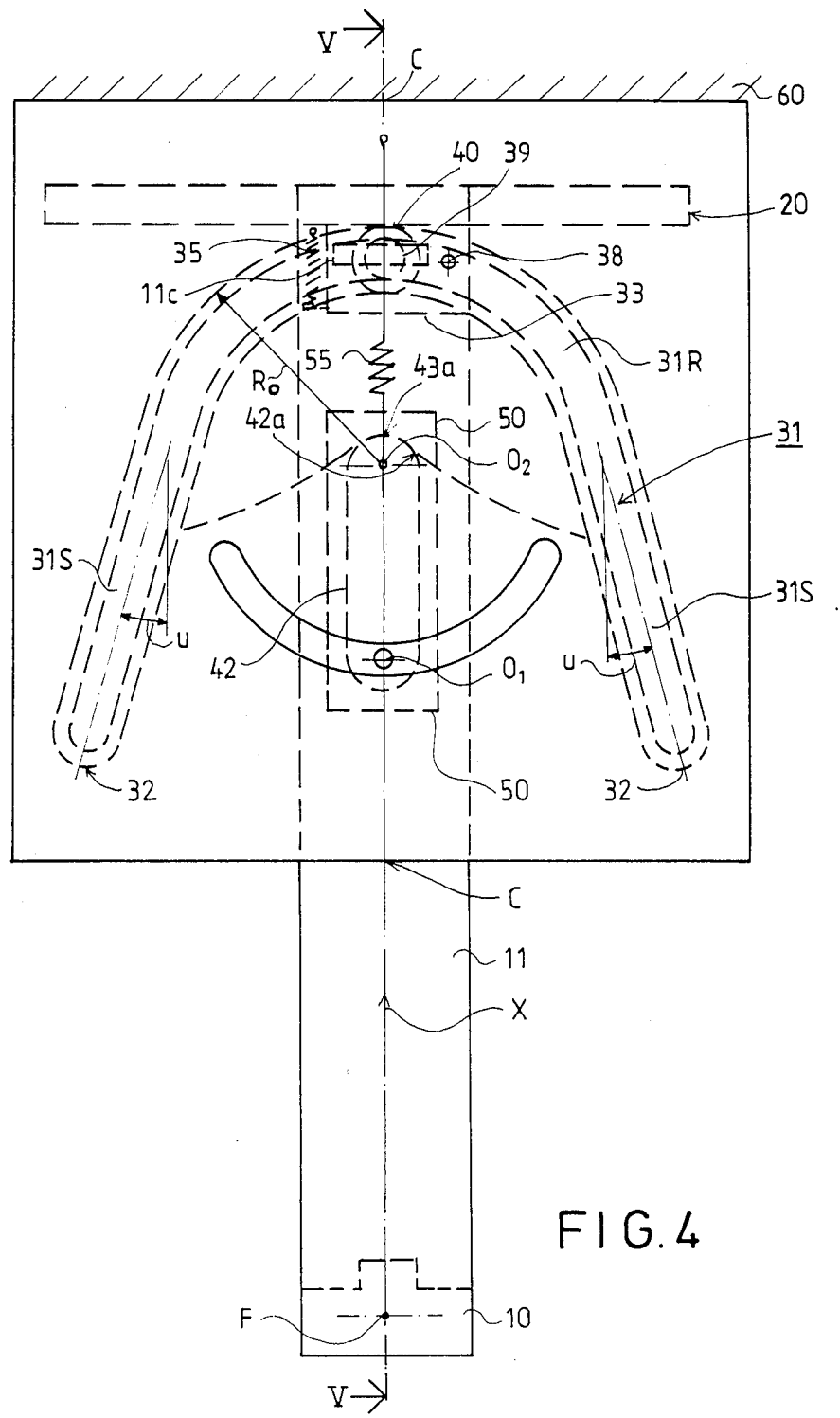
FIG. 4 is a view similar to FIGS. 2 and 3, illustrating a middle or central position of the present invention.

FIGS. 2-6 illustrate the movement of the X-ray tube 10 and the film 20, to accomplish the above-described represented projection and geometry. The design of an apparatus in accordance with the present invention will first be described with reference to FIGS. 2-6, followed by a more detailed description of the turning of the rotary frame 11, with respect to FIGS. 2, 3 and 4 illustrating different positions.

Figure 5:
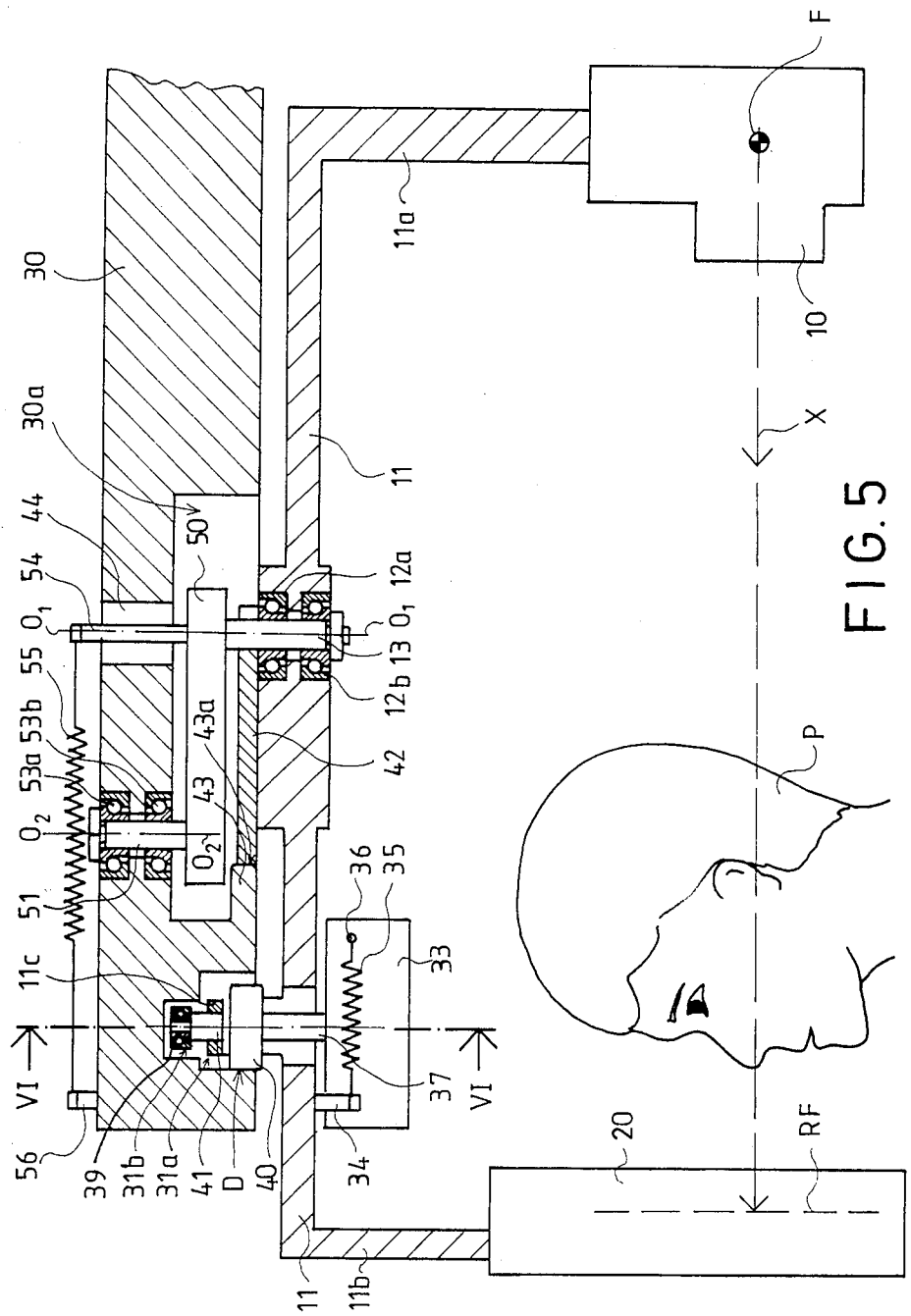
FIG. 5 is a vertical sectional view of a method and apparatus in accordance with the present invention, along line V—V in FIG. 4, illustrating the central or middle position in accordance with the present invention.

The apparatus of the present invention comprises a frame section 30, which is substantially stationary and fastened in a known manner such as to a base 60 on the floor. The base 60 may have provision for moving the frame section 30 to a suitable working height. The rotary frame or arm 11, rotated in a substantially horizontal plane, is suspended from the base 30 in a manner in accordance with the present invention. In other words, as illustrated for example in FIG. 4, the rotary frame 11 is essentially an elongated arm, having a vertical part 11b supporting a film cartridge 20 containing X-ray film RF, and a vertical part 11a supporting the X-ray tube 10 (FIG. 5). A drive mechanism and other known equipment which has not been illustrated, may also be supported on the arm 11, e.g. at the vertical part 11b.

The rotary frame 11 is suspended by way of bearings 12a and 12b (FIG. 5), to be rotatable about a vertical shaft $O_1$—$O_1$ of a crank 50. The vertical shaft $O_1$—$O_1$ is not fixed, but is, during the exposure, substantially horizontally swung with respect to the fixed frame 30. A rear journal pin 13 of the rotary frame 11 is fixedly fastened to the X-ray tube 10 end of the crank 50. At the other end of the crank 50, turning in space 30a of the frame 30, a front journal pin 51 is installed in bearings 53a, 53b associated with the fixed frame 30.

Both journal pins 13 and 51 have two opposite bevelled ball bearings 12a, 12b; 53a, 53b which are preloaded to be completely play-free, and carry both the axial loading due to the weight of the rotary frame 11, and the equipment attached to it, and also the radial force during the rotation of the rotary frame 11. Instead of bevelled ball bearings 12, 53, equivalent conical ball bearings or other similar combined axial and radial bearings may be utilized. It is important that the noted bearing system be well designed, correctly built, and properly installed, with a view towards the rotary mechanism.

In addition to the crank 50 and the journal pins 13 and 51, the rotary mechanism in accordance with the present invention also comprises a counter-profile 42 which is fixedly fastened to a top side of the rotary frame 11 (FIG. 5) so that one end of the counter-profile is about the vertical shaft 13. A round surface 42a of the other end of the rotary counter-profile 42 is, when the apparatus is in the middle or substantially central position illustrated in FIG. 4, at the journal pin 51. A guide profile 43, affixed to stationary frame 30, has a vertical guiding surface shaped as illustrated by the dotted lines in FIGS. 2, 3, 4. This guide profile 43 interacts with the round end surface 42a and the flat sides 42b of the counter-profile 42. The guide profile 43 is substantially symmetrical with respect to the center plane C—C (FIG. 4) and has a round recess 43a at the middle thereof. The round end 42a of the counter-profile 42 leans or abuts against this round recess 43a of the profile 43, contributing to the overall stability of the mechanism and apparatus when operating at or near the middle position illustrated in FIG. 4, and also at both adjacent sides of this position.

The counter-profile 42 is adapted to rotate when substantially centered at the middle position, as illustrated in FIG. 4. These guide surfaces of the profile 42 and the counter-profile 43 determine position of the instantaneous rotary center of the rotary arm 11. In other words, curvilinear guide surfaces 42a, 43a, precisely determine position of the instantaneous rotary center in the curved central region of the apparatus as illustrated in FIG. 4, while the straight side section 42b of the counter-profile 42 together with the curved side of the guide profile 43, move the rotary center when touching one another, thus increasing a turning radius of the rotary arm 11. Interaction of the counter-profile 42 with the guide profile 43 in the various operating positions, will be described in further detail below.

An important feature of the mechanism in accordance with the present invention, is the equipment and components with which rotating force is transmitted to the rotary frame 11. Such equipment comprises a guide groove 31 located in the fixed frame 30, and opening to the underside thereof. This guide groove 31 has a shape substantially similar to the principle shape of a jawbone and dental arch, taking into account the constant distance $b_0$-$b_5$ described in accordance with FIG. 1.

The guide groove 31 is substantially symmetrical with respect to the vertical center plane C—C, and has side sections 31S positioned at a narrow angle u with respect to the plane C—C and terminating at end sections 32. The groove 31 also has a curved section 31R connecting the side sections with one another. The curved section 31R has a section of a constant radius $R_0$ with a center point located on the vertical axis $O_2$, and two sections on which the radius of curvature R changes and smoothly becomes infinitely large, to turn into the straight sections 31S. In FIG. 1, one-half of the constant-radius section is represented by sector c, and one of the sections with the increasing radius of curvature is represented by sector d, on which the center of rotation moves from the axis $O_2$ to the axis $O_3$. Generally, the angle u is in the range of about 10°–20°. The guide groove 31 has a narrower internal or bottom section 31b and a broader outer or mouth section 31a, these sections 31a, 31b having substantially constant widths over the entire length of the groove 31. The guide groove 31 or similar rail system is shaped to make the exposed portion of the X-ray film RF in the film cartridge 20 pass the object being photographed at a constant distance $b_0$-$b_5$ so that the magnification ratio will remain essentially constant over the entire image field.

The groove 31 operates as a guide and drive block together with a drive unit 33 which is fastened to the rotary frame 11. An electrical motor serves as a drive motor in the unit 33, along with a transmission which turns the drive wheel 40 installed on a drive shaft 37 of the unit 33, as best viewed in FIG. 6. The unit 33 is pivotally suspended by a journal pin 38 associated with the rotary frame section 11. The unit 33 is biased or turned about the journal pin 38 to the driving position of the drive wheel 40, by a spring 35 installed between pins 34 and 36. The spring 35 provides a constant load onto the drive wheel 40, especially against an outer side of the drive (drawing) section 31a of groove 31. In FIG. 5, the point where the drawing or contact occurs is indicated by the reference character D. The width of the outer mouth section 31a is slightly broader than a diameter of the drive wheel 40 as illustrated.

Figure 6:
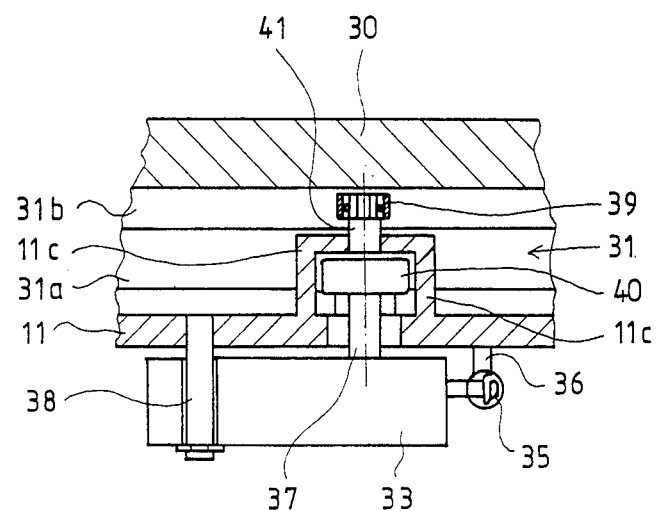
FIG. 6 is a sectional view along line VI—VI of FIG. 5.

As illustrated in FIGS. 5 and 6, the rotary frame 11 has a protruding part 11c at the drive wheel 40, which reaches over the top of the drive wheel 40 as illustrated. A journal pin 41 is attached to the side of the protruding part 11c, with a guide wheel 35 being positioned at an end of the journal pin 41. The journal pin 41 is loaded to make the guide wheel 39 contact or lean against an inner side of the guide section 31b of the groove 31. This inner side is opposite to the side against which the drive wheel 40 is loaded to lean or abut on the section 31a of the groove 31. The drive wheel 40 and the guide wheel 31 are preferably arranged coaxially, i.e. so as to make the centers of rotation thereof unite. Then, the loading spring 35 will not generate any extra torque which might disturb the rotary movement.

FIGS. 2, 3 and 4 illustrate favorable location of the spring element 35 of the driving unit 33. The spring element 35 is preferably located at the opposite end of the unit 33 from the journal pin 38, so that the spring 35 and the shaft 38 are substantially situated symmetrically on both sides of the longitudinal center plane of the rotary frame 11.

As illustrated in FIG. 5, a pin 54 is situated at the rear journal pin 13 of the crank 50, and extends through a groove 44 of the fixed frame 30 out of the top side of the frame. A spring 55 is fastened to the pin 54, with the opposite end of the spring being fastened to the fixed frame 30.

An important feature of the drive mechanism is that the drive unit 33, together with the loading spring 35, ensures that the drive wheel 40 follows the outer edge of the drive (drawing) section 31a of the groove 31, and that the guide wheel 39 similarly follows, play-free, the inner edge of the guiding section 31b, in all positions of the rotary frame 11. This provides a play-free, smooth, reliable, and jerkless drive in all positions of the rotary frame 11.

The journal pin 38 and the spring element 35 of the drive unit 33, are arranged on opposite sides of a passing point of the X-ray X so that the spring 35 loads the unit 33 towards the X-ray film cartridge 20, and towards the outer side of the guide groove 31a.

Operation of the illustrated embodiment of the present invention will now described with reference to FIGS. 2, 3 and 4 which illustrate operation of the turning crank mechanism. The description of this operation begins at the middle position illustrated in FIG. 4. However, the apparatus, i.e. rotary arm 11, usually begins movement from an end position 11' of the rotary frame 11, with the rotary frame 11 turning through the intermediate position illustrated in FIG. 3, to the middle position illustrated in FIG. 4, and then proceeding, as guided by the right-hand section of the groove 31, to the opposite end position corresponding to FIG. 2. At both sides of the middle position illustrated in FIG. 4, in other words on the sector c between the radii $a_0$ and $a_2$ illustrated in FIG. 1, the rotary frame 11 is rotated about the rotary axis $O_2$ by interaction of the curved, constant radius section 31R of the groove 31, the drive wheel 40, and the guide wheel 39. In this position, the crank 50 is substantially parallel with the arm 11, and the rotary axes $O_1$ and $O_2$ of the journal pins 13 and 51 are situated in the vertical center plane C—C of the rotary frame 11.

In order to make the center position of the crank mechanism 11, 13, 50, 51 and 30 controlled and precise, the mechanism additionally comprises the counter-profile 42, whose guiding end 42a abuts or leans play-free against the round recess 43a of the guide profile 43 affixed to the frame 30. Then the parts 42a and 43a, will define the stable center of rotation of the mechanism. When the mechanism begins to rotate from the middle position illustrated in FIG. 4, for instance towards the intermediate position illustrated in FIG. 3, then the center of rotation $O_2$ determined by the parts 42a and 43a, will remain on the constant-radius section 31R of the guide groove 31. The shape of the groove 31 resembles the shape of a jawbone.

When the guide wheel 39 and the drive wheel 40 pass from the constant-radius $R_0$ section of the groove 31 to the increasing-radius section, the center of rotation of the rotary frame 11 begins to move from the center $O_2$ and the center plane C—C, towards the side, which occurs so that the crank 50 begins to turn non-parallelly with respect to the rotary frame 11, and the straight vertical side 42b of the counter-profile 42 leans or abuts against the curved side of the guide profile 43 tangentially touching the same, and possibly sliding therealong, so that this tangent rolls and conceivably also slides from the recess 43a of the guide profile 43, to the side section of the guide profile 43, while the center of rotation of the rotary frame 11 simultaneously, continuously, and smoothly moves from the axis $O_2$ to the axis $O_3$.

On this area (sector d in FIG. 1), the rotary frame 11 of the crank 50 horizontally turns in the same direction. When moving from the position of FIG. 3 to the position illustrated in FIG. 2 (sector e in FIG. 1), the crank 50 turns in a direction opposite to the turning direction of the rotary frame 11. In the area of the straight guide grooves 31S, the counter-profile 42 does not operate. In the front area of the dental arch, i.e. when the rotary frame 11 turns about the axis $O_2$, the exact location and smooth movement of the center of rotation from one control phase to another is ensured, additionally by way of the counter-profile 42 and the guide profile 43, and also by the guide spring 55. The guide spring 55 is positioned between the pin 54 protruding through the groove 44 of the fixed frame 30, and a pin 56 of the frame 30. The spring 55 ensure that the guide profile 43 and the counter-profile 42 remain at all times in stable contact with one another, when operating in the area 31R of the groove 31.

Only one feasible embodiment of the present invention has been described above. The details of this particular embodiment may vary in many ways within the framework of the present invention. For example, instead of the guide groove 31, it is possible to use, for example, a guide rail having a shape corresponding to the shape of the guide groove 31, and which may be arranged to operate, for example, so that the drive wheel 40 rolls against one side thereof and the guide wheel 39 rolls against the opposite side thereof. The drive wheel 40 and the guide wheel 31 are preferably coaxially positioned on the same vertical shaft, so that the rotary frame 11 may move without any axial loading disturbing the smooth, play-free and jerkless drive of the drive wheel 40.

Stable drive and stable control may also be ensured in this manner. The drive unit 33 may also be arranged in some other manner than what is particularly illustrated in the figures, with the spring loading generated in different ways. The details of the crank mechanism may also vary and differ from what has been described above. The drive device and the crank mechanism, i.e. the guide and drive device, drive unit, and crank means, are so interassembled that the turning of the rotary frame 11 occurs practically without any play or jerks.

The method and apparatus in accordance with the present invention provide especially feasible shape of the running path of the exposed area of the film RF, marked in FIG. 1 as "A" with a dotted line, along with the other advantages discussed above, cooperatively connected with both the operation of the device and the mechanical design thereof.

An embodiment of the present invention has been described in which the drive groove 31 is situated in the fixed section 30 and the drive unit 33 is situated in the rotary frame or arm 11. In some special situations, it may be possible to locate the drive unit 33 on the fixed frame 30, and the drive groove or guide rail 31 on the rotary frame 11, in which case the drive unit 33 and the drive groove or similar structure have changed positions. However, the embodiment illustrated above is presently the best mode for carrying out the present invention.

The preceding description of the present invention is merely exemplary, and is not intended to limit the scope thereof in any way.

What is claimed is:

1. A panoramic tomography X-ray apparatus, especially for dental photography, having a fixed frame and a rotary frame suspended from the fixed frame, the rotary frame having an X-ray tube at one end thereof and a film cartridge device for X-ray film at an opposite end thereof, with an object to be photographed adapted to be positioned between the X-ray tube and the film cartridge, and the rotary frame being situated to be rotatable in a plane for taking panoramic X-ray photographs, said apparatus comprising drive means for rotating said rotary frame about the plane, said drive means comprising a drive and guide device being a groove or rail substantially symmetrical with a center plane of said apparatus, said drive and guide device comprising substantially straight side sections and a curved section interconnecting said side sections, and a drive unit situated to interact with said drive and guide device, said drive unit comprising a drive wheel for turning said rotary frame, and crank means for suspending said rotary frame from said fixed frame, said crank means connected with said rotary frame adjacent the X-ray tube end thereof through one axis, and with said fixed frame at an opposite end thereof through a second axis, such that when said rotary frame is substantially centered in said apparatus, said two axes are substantially positioned along said center plane of said apparatus, wherein said crank means additionally comprise a counter-profile affixed to a top side of said rotary frame, a guide profile affixed to an opposite bottom side of the fixed frame, said guide profile having a guide surface substantially symmetrical with respect to said center plane of said apparatus, and substantially concentric to said second axis of said crank means, said counter-profile also comprising a guide surface for contacting said profile guide said drive means and crank means situated to interact with one another such that when said drive unit passes around said curved section of said drive and guide device, said rotary frame turns about said second axis, and when said drive unit is guided along said straight sections, said rotary frame simultaneously turns about both said first and second axes.

2. The apparatus of claim 1, wherein said drive and guide device being shaped such that an exposed portion of the X-ray film in the cartridge pass the object being photographed at a constant distance, whereby magnification can be maintained substantially constant over the entire panorama.

3. The apparatus of claim 1, wherein said drive unit additionally comprises a guiding block situated to contact an edge of said guide and drive device opposite an edge contacted by said drive wheel.

4. The apparatus of claim 3, wherein said guiding block is a guide wheel situated substantially coaxially with said drive wheel.

5. The apparatus of claim 1, wherein said crank means additionally comprise
   a first set of bearings through which said first axis is connected with said rotary frame, and
   a second set of bearings through which said second axis is connected with said fixed frame.

6. The apparatus of claim 5, wherein said bearings are bevelled ball bearings.

7. The apparatus of claim 5, wherein said bearings are pre-loaded to be substantially play-free, and simultaneously carry
   axial loads due to weight of said apparatus and radial forces during rotation.

8. The apparatus of claim 4, wherein said drive and guide device is constituted by a groove opening to an underside of said fixed frame,
   and said drive unit additionally comprises
   a substantially vertical axis about which said drive unit turns, and
   a spring element for loading said drive wheel against an outer edge of said groove, and
   said rotary frame having a protruding part to which said guide wheel is fastened.

9. The apparatus of claim 8, wherein said guide groove comprises
   a narrower inner section for receiving said guide wheel, and
   a broader outer section for receiving said drive wheel, said outer section being slightly wider than a diameter of said drive wheel.

10. The apparatus of claim 8, wherein said drive unit axis and said spring element are situated on opposite sides of the path of an X-ray, said spring element loading said drive unit towards the X-ray film cartridge and towards an outer side of said guide groove.

11. The apparatus of claim 1, wherein said curved section of said drive and guide device is of substantially constant radius of curvature and said drive and guide device additionally comprising,
   two sections in which the radius of curvature changes and smoothly becomes infinately large,
   each said section connecting said curved section with a respective straight side section of said drive and guide device,
   with a center of rotation of said rotatable frame being substantially constant on said center plane of said apparatus, when said drive unit passes around said curved section of said substantially constant radius, and
   said center of rotation of said rotatable frame smoothly moving away from said center plane in a curved path, as said drive unit passes along one of said sections of changing radius of curvature.

12. The apparatus of claim 1, wherein
said counter-profile guide surface comprises a curved portion and a substantially straight portion, said counter-profile situated to rotate when said curved surface portion contacts said profile guide surface, and said straight surface portion situated to tangentially contact said profile guide surface, whereby a turning radius of said rotary frame increases.

13. The apparatus of claim 12, additionally comprising
   a spring element connected to the stationary frame and to said crank means, said spring element biasing said counter-profile to be in stable contact with said guide profile, thereby ensuring smooth increase of said turning radius of said rotary frame.

14. The apparatus of claim 13, additionally comprising
   a pin for affixing one end of said spring element to said first axis of said crank means, and
   said stationary frame comprising a groove through which said pin is situated.

15. The apparatus of claim 1, wherein an angle of said side sections of said drive and guide device with respect to said center plane is between about 10°–20°.

16. The apparatus of claim 12, wherein said profile and counter-profile are positioned with respect to one another,
   with said curved portion of said counter-profile guide surface contacting said profile guide surface when said drive unit passes around said curved section of said drive and guide device which is of substantially constant radius of curvature, and
   said substantially straight portion of said counter profile guide surface tangentially contacting a curved part of said profile guide surface as said drive unit is guided towards one of said straight sections of said drive and guide device,
   whereby a center of rotation of said rotatable frame smoothly moves away from said center plane of said apparatus.

17. The apparatus of claim 12, wherein said profile guide surface is substantially in the shape of a bell curve.

18. A method for taking panoramic photographs, such as X-rays of teeth, comprising the steps of
   situating film and a photographic energy source on opposite sides of an object to be photographed,
   rotating the source about a center of rotation substantially situated on a center plane of the rotational arc, and
   gradually shifting the center of rotation as the source moves away from the center plane, wherein the center of rotation is gradually shifted by the step of
   moving a support for the source along a groove or rail that is substantially symmetrical with respect to the center plane, curvilinear adjacent the center plane, and substantially straight away form the center plane,
   wherein the support is moved along the groove or rail through crank means comprising two axes,
   with said support rotating about one of said axes when moving along the curved portion of the groove or rail, and
   said support simultaneously turning about both said axes when moving along one of the straight portions of the groove or rail.

19. The method of claim 18, wherein the crank means additionally comprise a counter-profile having a straight portion and a curved portion,
   and the support is moved along the guide or rail by the additional steps of
   the curved portion of the counter-profile engaging a guide profile during rotation of the support about the one of both axes, and
   the straight portion of the counter-profile engaging the guide profile during rotation of the support about both the axes.

* * * * *